United States Patent [19]

Gunkel

[11] Patent Number: 5,138,085
[45] Date of Patent: Aug. 11, 1992

[54] PROCESS FOR PURIFYING POLYBROMINATED TRIARYL PHOSPHATE ESTERS

[75] Inventor: Louis T. Gunkel, Yardley, Pa.

[73] Assignee: FMC Corporation, Philadelphia, Pa.

[21] Appl. No.: 706,133

[22] Filed: May 28, 1991

[51] Int. Cl.$^5$ ............................................... C07F 9/12
[52] U.S. Cl. .................................... 558/146; 558/211
[58] Field of Search ................................. 558/146, 211

[56] References Cited

U.S. PATENT DOCUMENTS

| | | | |
|---|---|---|---|
| 1,866,852 | 7/1932 | Hand et al. | 558/150 |
| 2,561,493 | 7/1951 | Caprio et al. | 106/177 |
| 2,894,015 | 7/1959 | Kyker | 260/461 |
| 3,436,441 | 4/1969 | Thompson | 260/966 |
| 3,526,681 | 9/1970 | English | 260/949 |
| 3,945,891 | 3/1976 | Aal et al. | 203/77 |
| 4,059,655 | 11/1977 | Crano | 558/144 |
| 4,897,502 | 1/1990 | Gunkel et al. | 558/102 |

FOREIGN PATENT DOCUMENTS 50-47953  4/1975  Japan.
1168819  10/1969  United Kingdom.

OTHER PUBLICATIONS

Wiberg, K. B. Laboratory Technique in Organic Chemistry; McGraw-Hill, 1960; pp. 98–104.

*Primary Examiner*—Robert W. Ramsuer
*Assistant Examiner*—Michael G. Ambrose
*Attorney, Agent, or Firm*—R. E. Elden; F. Ianno; R. L. Andersen

[57] ABSTRACT

The invention is a process for purifying a solid, storage-stable tris(bromophenyl)phosphate ester dissolving a crude tris(bromophenyl)phosphate in an ester at an elevated temperature, and cooling the solution sufficiently to recover a solid phase.

8 Claims, No Drawings

PROCESS FOR PURIFYING POLYBROMINATED TRIARYL PHOSPHATE ESTERS

The invention is a process for purifying solid tris(-bromophenyl)phosphate esters.

U.S. Pat. No. 3,945,891 to Aal et al. discloses that aryl phosphate esters are generally made by reacting an excess of a C1 to C4 alkyl phenol with phosphorus oxychloride in the presence of a catalyst, such as, aluminum chloride or magnesium chloride. The patent discloses that increasingly more stringent limitations are being placed upon the allowable amount of unreacted and/or free phenols in the products. These requirements have created a demand for manufactured alkylated triaryl phosphate ester products containing less than the 500 to 3000 parts per million phenol previously available commercially.

The crude mixture resulting from the reaction of a phenol, or substituted phenol with phosphorus oxychloride is usually dark in color, and contains an excess of phenols, partially reacted phosphorochloridates (mono or di substituted $POCl_3$) and catalyst residues (if used).

U.S. Pat. No. 3,945,891 discloses alternative processes employed to remove any excess phenolics included caustic washing, permanganate oxidation, treatment with solid adsorbents and the like. Avoidance of these economically unattractive processing steps was achieved instead by an improved distillation process which could reduce the concentration of volatile phenol or alkylated phenol to 100 ppm.

U.S. Pat. No. 4,897,502 to Gunkel et al. discloses that a tri(haloaryl) phosphate ester that is a solid under ambient conditions usually is purified by recrystallization from an aromatic solvent such as toluene or xylene. Such a process is undesirable because the recrystallization steps are costly and the yield of product is reduced. The process usually necessitates further work up of crude product from the solvent mother liquor. Instead the patent teaches a process in which the reaction mixture is dissolved into an alcohol with a Hildebrand solubility parameter between 20 and 23 SI units and a Hansen dispersion coefficient between 14.2 and 15.5 SI units. On cooling, a pure solid product is recovered in high yield containing less than 100 ppm halophenol.

U.S. Pat. No. 2,561,493 discloses that solid chlorinated triphosphate esters can be recovered in a pure form by reacting the appropriate phenol with phosphorus oxychloride, distilling the product under vacuum, and recrystallizing the solid distillate by crystallizing from an equal volume of hexane or a mixture of ethyl alcohol and acetone. However, this method is not satisfactory for tris(bromophenyl)phosphate esters because of their extreme insolubility in alkanes, such as hexane and because they will transesterify in the presence of alcohols, increasing the halophenol concentration in the product and also form a mixed alkyl-aryl ester.

The present invention is a process for purifying solid tris(bromophenyl)phosphate comprising dissolving the crude tris(bromophenyl)phosphate ester into an ester at an elevated temperature to form a solution, the ester consisting essentially of a C2 to C6 monohydroxy aliphatic alcohol and a C2 to C6 monocarboxylic aliphatic acid, cooling the solution of the tris(bromophenyl)phosphate sufficiently to yield a solid phase, and separating the solid phase as tris(bromophenyl)phosphate containing less than 50 ppm bromophenol.

The process is suitable for purifying any solid, tris(-bromophenyl)phosphate, such as, tris(2-bromophenyl)phosphate, tris(3-bromophenyl)phosphate, tris(4-bromophenyl)phosphate, tris(2,4-dibromophenyl)phosphate, tris(2,4,6-tribromophenyl)phosphate, or the like. Preferably the process is useful for purifying tris(2,4-dibromophenyl)phosphate which is known to be useful as a flame retardant.

The crude tris(bromophenyl)phosphate can be incorporated into the ester solvent at any time after the completion of the reaction.

Clearly the desirable "elevated temperature" is a function of the ester and tris(bromophenyl)phosphate as well as the equipment being employed for the operations and can be determined by one skilled in the art without undue experimentation. Preferably, the temperature selected is sufficiently high to dissolve substantially all of the tris(bromophenyl)phosphate to form a solution that on cooling results in a maximum yield of purified tris(bromophenyl)phosphate. When the dissolved reaction mixture is vented to the atmosphere, it is usually desirable if the temperature is maintained at or somewhat less than the reflex point of the mixture.

One skilled in the art will readily recognize that the boiling point of the ester may be a factor in selecting the optional hydrocarbon solvent mixture. Further, one skilled in the art will recognize that ester may be either a pure ester, such as ethylacetate or a mixture of homologeous esters or of isomers, such as a mixture of n-hexyl acetate and isohexyl acetate.

Surprisingly, it was observed that the tris(bromophenyl)phosphate made by the claimed process was substantially free from impurities, such as bromophenols and mixed esters as the tris(bromophenyl)phosphate made by the process of copending patent application Ser. No. 706,132 filed May 28, 1991. Such impurities would normally be expected as a consequence of transesterification between the ester solvent and the crude tris(bromophenyl)phosphate.

Although the invention is exemplified below in terms of the preferred tris(2,4-dibromophenyl)phosphate, it is not intended to limit the scope of the invention to that specific compound.

Preparation of crude tris(2,4-dibromophenyl)phosphate:

A phosphorylation reaction was run by charging 1500 grams of 2,4-dibromophenol and 3.75 grams of magnesium chloride into a two-liter flask equipped with stirrer, thermometer, reflux condenser, heating mantle, and a caustic scrubber to absorb HCl byproduct. This mixture was heated to 120° C. and 319.6 grams of phosphorus oxychloride were added over a two hour period. At the end of the phosphorus oxychloride addition, the mixture was heated to 160° C. and held for three and one-half hours. The end of the reaction was determined when the 2,4-dibromophenol remaining in the reaction mixture remained constant and the analysis showed the absence of any measurable amounts of partial phosphate esters, and chloridates. The analysis of the crude mixture showed 0.28% 2,4-dibromophenol and 99.4% ester product. A crude product weight of 1545 grams was obtained.

EXAMPLE 1

Ethyl Acetate

Two hundred and fifty-five grams of the crude ester product above was dissolved in 726 grams of ethyl acetate at 75° C. to yield a clear solution. The mixture was then cooled slowly. At 50° C., crystals began to appear in the solution. When the temperature reached 25° C., the slurry was separated in a stainless steel centrifuge. Seven hundred and four grams of mother liquor were recovered which contained 0.06% 2,4-dibromophenol, 6.07% product and 0.34% chloridates.

The wet cake weighed 200 grams and the product dried to a weight of 192 grams. The product had a melting point of about 100° C. and contained 14 ppm of 2,4-dibromophenol. Recovery from ethyl acetate was 75%.

EXAMPLE 2

Isopropyl Acetate

Two hundred and fifty-eight grams of the crude product described above were dissolved in 602 grams of isopropyl acetate at 87° C. The mixture was then cooled slowly to 30° C. to form a slurry of white crystals. The slurry was separated by a basket centrifuge. The product when dried in a vacuum oven, weighed 196.82 grams of product, a 76% yield. The amount of solvent remaining in the product after drying was 300 ppm.

The 605 g of mother liquor comprised 93% solvent and 7% solids consisting of 0.2% 2,4-dibromophenol and 41 g of phosphate ester product (16%).

EXAMPLE 3

Butyl Acetate

Two hundred and fifty-one grams of the crude product were heated with 586 grams of butyl acetate as above. At 30° C., the "wet" cake weighed 206.5 grams and the product weighed 180.72 grams after drying, a 72.7% yield. The 2,4-DBP level in the product was 42 ppm.

EXAMPLE 4

Ethyl Acetate

A batch of crude tris(2,4-dibromophenyl)phosphate was prepared as above yielding 2109 grams of 98% product. A 205 g portion was dissolved in 651 g ethyl acetate on heating to 78° C. The dried crystals weighed 148 g, a 73.6% yield. The mother liquor contained 47.4 g product or 23.6% of the feed.

EXAMPLE 5

Comparison of Ethyl Acetate and Pentyl Alcohol (U.S. Pat. No. 4,897,502)

In this experiment crude phosphorylation product similar to that of Example 4, containing 0.2% excess 2,4-dibromophenol was divided and crystallized from both ethyl acetate and pentyl alcohol for comparison. From Table I it can be seen that the filtrate from the pentyl alcohol mother liquor contains more 2,4-dibromophenol than the corresponding ethyl acetate mother liquor (even though somewhat more solvent was employed in the pentyl alcohol comparison). This is because the pentyl alcohol reacts with the product, tris (2,4-dibromophenyl)phosphate to transesterify, forming pentyl bis(2,4-dibromophenyl)phosphate and releasing a molecule of 2,4-DBP for each mole of alcohol reacted. The mixed ester appears in both the mother liquor and the product and represents impurities and loss in the process. The mixed ester product does not appear in either the ethyl acetate mother liquor or product.

EXAMPLE 6

Reuse of Solvent

This example illustrates that an ester can be reused as a solvent at least ten times before requiring clean up. Crude tris(2,4-dibromophenyl)phosphate was prepared by the phosphorylation process described above. The 2,4-dibromophenol used as a raw material assayed 99.5% and contained 0.3% tribromophenol and 0.2% monobromophenol. The crude reaction mixture assayed 99.5% and contained 0.6% excess 2,4-dibromophenol with traces of chloridates and tribromophenol. Ten 250 g batches of crude material were purified with 500 g ethyl acetate as the solvent (which was reused). Table II illustrates the percent yield and product quality (ppm 2,4-dibromophenol, brightness and color) of the tris(2,4-dibromophenyl)phosphate and of the build up of impurities in the mother liquor. At the end of the first (and tenth) cycle respectively, the mother liquor contained 90.7% (77.3%) ethylacetate; 0.18% (7.55%) DBP (2,4-dibromophenol); 0.04% (0.72%) TBP (2,4,6-tribromophenol); 0.0% (0.25%) dichloridate; 0.0% (3.07%) monochloridate; 1.9% (3.6%) monobromophenyl bis(2,4-dibromophenyl phosphate); 0.21% (0.18%) tribromophenyl bis(2,4-dibromophenyl phosphate) and 6.6% (4.6%) tris (2,4-dibromophenyl)phosphate (the product).

As can be seen from Table II the overall yield increases from about 75% after the first cycle to average about 88% after 6 to 10 cycles; the product quality as measured by dibromophenolic content, brightness and yellowness remains uniformly high throughout as many as ten cycles.

TABLE I

| COMPARISON OF ETHYL ACETATE AND PENTYL ALCOHOL AS A SOLVENT | | |
|---|---|---|
|  | Ethyl Acetate | Pentyl Alcohol |
| Weight crude tris (2,4-dibromophenyl) phosphate | 300 g | 306 g |
| Weight solvent | 595 g | 490 g |
| Filtrate Weight | 506 g | 423 g |
| Analysis |  |  |
| % Solvent | 95.4% | 97.8% |
| % 2,4-DBP* | 0.04% | 0.08% |
| % Mixed Ester | None | 0.42% |
| % Product | 4.5 g | 1.3 g |
| Weight Wet Cake | 283 g | 423 g |
| Dry Product Weight | 231 g | 268 g |
| Analysis |  |  |
| % 2,4-DBP | None Detected | 0.06% |
| % Mixed Ester | None Detected | 0.42% |
| % Product | 100% | 99.5% |

*2,4-DBP = 2,4-dibromophenol

TABLE II

| PRODUCT QUALITY ON MOTHER LIQUOR RECYCLE | | | | | | | |
|---|---|---|---|---|---|---|---|
|  |  |  |  |  | Mother Liquor | | |
| Cycle No. | Yield % | DBP ppm | Color | | % ETOAC* | % Phenols | % Chloridates |
|  |  |  | Br. | Yell. |  |  |  |
| 1 | 75.5 | 17 | 96.0 | 0.63 | 90.7 | 0.2 | 0.0 |
| 2 | 93.5 | 16 | 96.3 | 0.95 | 89.1 | 0.6 | <0.1 |
| 3 | 87.1 | >5 | 95.5 | 0.52 | 89.5 | 0.6 | <0.1 |
| 4 | 85.6 | >5 | 97.2 | 0.55 | 88.0 | 1.2 | 0.1 |
| 5 | 85.9 | 17 | 96.5 | 1.94 | 84.0 | 2.8 | 2.1 |
| 6 | 92.0 | 21 | 97.0 | 1.95 | 84.3 | 3.1 | 1.5 |
| 7 | 98.7 | 36 | 97.4 | 1.81 | 84.6 | 3.7 | 1.7 |
| 8 | 79.1 | 22 | 96.3 | 2.09 | 77.6 | 8.4 | 3.6 |
| 9 | 81.2 | 20 | 96.6 | 1.91 | 80.1 | 7.3 | 2.6 |

TABLE II-continued

PRODUCT QUALITY ON MOTHER LIQUOR RECYCLE

| Cycle No. | Yield % | DBP ppm | Color Br. | Color Yell. | % ETOAC* | Mother Liquor % Phenols | Mother Liquor % Chlorides |
| --- | --- | --- | --- | --- | --- | --- | --- |
| 10 | 95.5 | 20 | 97.1 | 1.95 | 77.3 | 9.2 | 3.3 |

*ETOAC = ethyl acetate solvent

I claim:

1. A process for purifying solid tris(bromophenyl)phosphate comprising dissolving the crude tris(bromophenyl)phosphate into an ester at an elevated temperature to form a solution, the ester consisting essentially of a C2 to C6 monohydroxy aliphatic alcohol and a C2 to C6 monocarboxylic aliphatic acid, cooling the solution of the tris(bromophenyl)phosphate sufficiently to yield a solid phase, and separating the solid phase as tris(bromophenyl)phosphate containing less than 50 ppm bromophenol.

2. The process of claim 1 wherein the elevated temperature is the reflux temperature of the solution of crude tris(bromophenyl)phosphate in the ester.

3. The process of claim 1 wherein the ester is ethyl acetate.

4. The process of claim 2 wherein the ester is ethyl acetate.

5. The process of claim 1 wherein the tris(bromophenyl)phosphate is tris(2,4-dibromophenyl)phosphate.

6. The process of claim 2 wherein the tris(bromophenyl)phosphate is tris(2,4-dibromophenyl)phosphate.

7. The process of claim 3 wherein the tris(bromophenyl)phosphate is tris(2,4-dibromophenyl)phosphate.

8. The process of claim 4 wherein the tris(bromophenyl)phosphate is tris(2,4-dibromophenyl)phosphate.

* * * * *